(12) United States Patent
Lin et al.

(10) Patent No.: US 9,045,513 B2
(45) Date of Patent: Jun. 2, 2015

(54) METHOD FOR PREPARING PRECURSOR USED FOR LABELING HEPATOCYTE RECEPTOR AND CONTAINING TRISACCHARIDE AND DTPA LIGAND

(75) Inventors: Chih-Yuan Lin, Kinmen County (TW); Yu Chang, Taipei (TW); Jen-Tsung Wang, Changhua County (TW); Cheng-Fang Hsu, Taoyuan County (TW); Wei-Ti Kuo, Kaohsiung (TW); Hung-Wen Yu, Taoyuan County (TW); Wuu-Jyh Lin, Taoyuan County (TW); Mei-Hui Wang, Taoyuan County (TW)

(73) Assignee: Atomic Energy Council—Institute of Nuclear Energy Research, Taoyuan County (TW)

( * ) Notice: Subject to any disclaimer, the term of this patent is extended or adjusted under 35 U.S.C. 154(b) by 238 days.

(21) Appl. No.: 13/571,731

(22) Filed: Aug. 10, 2012

(65) Prior Publication Data
US 2014/0046045 A1    Feb. 13, 2014

(51) Int. Cl.
C07H 15/04    (2006.01)
C07H 1/06    (2006.01)
C07K 1/13    (2006.01)

(52) U.S. Cl.
CPC .................. *C07H 1/06* (2013.01); *C07H 15/04* (2013.01); *C07K 1/13* (2013.01)

(58) Field of Classification Search
None
See application file for complete search history.

(56) References Cited

PUBLICATIONS

Lee et al. Bioorganic & Medicinal Chemistry 19 (2011) 2494-2500.*

* cited by examiner

*Primary Examiner* — Layla Bland
(74) *Attorney, Agent, or Firm* — Rosenberg, Klein & Lee

(57) ABSTRACT

A method for preparing a precursor used to label hepatocyte receptors is revealed. The precursor contains a bifunctional structure including trisaccharide and DTPA ligand. During synthesis processes of the precursor, silica gel columns and Reverse phase-18 (RP-18) columns are used for purification. Thus both the purification times and cost of each purification are reduced. Moreover, use diethyl ether to facilitate precipitation of products and remove a part of coupling reagent. Removing the coupling reagent helps purification of products. Furthermore, $N^\alpha,N^\alpha$-bis(carboxymethyl)-L-lysine hydrate and benzyl chloroformate are coupled to form a trisaccharide skeleton so as to ensure the yield rate of trisaccharide structure.

9 Claims, 6 Drawing Sheets

METHOD FOR PREPARING PRECURSOR USED FOR LABELING HEPATOCYTE RECEPTOR AND CONTAINING TRISACCHARIDE AND DTPA LIGAND

BACKGROUND OF THE INVENTION

1. Fields of the Invention

The present invention relates to a method for preparing a precursor used for labeling hepatocyte receptors, especially to a method for preparing a precursor used for labeling hepatocyte receptors and containing bifunctional structure including trisaccharide and DTPA ligand.

2. Descriptions of Related Art

There are no nerves in the liver. Thus most people with liver diseases have no feelings or specific symptoms until their liver disease is at a late stage. Once there are some symptoms and people go to hospital for diagnosis, they already have serious hepatocirrhosis and liver cancer. Thus early diagnosis and treatment of liver diseases are so important to saving lives. Early detection of liver fibrosis will benefit the prevention of the liver diseases. Thus the early detection of liver diseases has received an enormous amount of attention in medical research.

The most common test for liver fibrosis is to get liver biopsy through liver puncture. This is an invasive test associated with the risk of sampling error and morbidity. Thus non-invasive tests to assess liver fibrosis have been developed and proposed by various research teams and institutions to assess the severity of hepatic fibrosis. One of the most promising ways is to use isotope tracer technique for detecting diseases or functional disorders. The isotope tracer technique is safe, painless (non-invasive), convenient and accurate. Moreover, due to fast development of techniques for molecular images, Positron Emission Tomography and Single-photon Emission Computed Tomography (SPECT) can provide functional diagnosis. In recent years, computed tomography (CT) and magnetic resonance imaging (MRI) are also used to overcome shortcomings of PET or SPECT on anatomical imaging.

Human cells have specific receptors on their surfaces to accept specific proteins or peptides. According to the specificity, some specific proteins or peptides are labeled with radioactive nuclides in advance and then delivered into human bodies. The labeled proteins or peptides will achieve higher concentration in specific organs or tissues so as to treat diseases or for diagnosis.

There are about two hundred thousand asialoglycoprotein receptors (ASGPR) on surfaces of mammalian hepatocytes. The ASGPR also has high affinity to galactose (Gal) and N-acetylgalactosamine (GalNAc). Especially ground substances that contain tri-Gals or substrate with tri-GalNAc have a high affinity for ASGPR on surfaces of hepatocytes, almost $10^6$ times of a single saccharide. Moreover, the affinity varies due to the length of a single chain. For example, the affinity of DCM-Lys(G-ah-GalNAc)$_3$ to hepatocytes is 12 times than the affinity of DCM-Lys(ah-GalNAc)$_3$ to hepatocytes even there is only a difference of a Glycine. In accordance with the above affinity and specificity, not only the drug targeting is improved, the amount of the drug used is minimized to nM level. Furthermore, based on the above biomedical character, Glyco-drugs are labeled with radioactive isotopes. Used together with nuclear imaging machines, a non-invasive and quantitative liver function test technique is available and this is beneficial to prevention and treatment of liver diseases.

In some papers, a method for synthesis of DTPA-aha-DCM-Lys(G-ah-GalNAc)$_3$ is revealed. But the synthesis processes are complicated and time-consuming. Refer to FIG. 1, during the synthesis, the trisaccharide skeleton is obtained by $N^\epsilon$-benzyloxycarbonyl-L-lysine and bromoacetic acid reacting in sodium hydroxide solution. However, it is not assured that amino group is exactly connected to two carboxylic acids. If there is only one carboxyl acid group connected, disaccharide is formed in following synthesis processes, instead of trisaccharide.

Moreover, there are two times of Sephadex gel chromatography such as Sephadex LH20 or Sephadex G-15 during the synthesis and the cost is expensive. Alcohol or acetic acid solution is used as elution solution for purification. The concentration time is increased due to the acetic acid solution. Moreover, hydroxide ion exchange resin is used to remove impurities completely. It's time and cost consuming are not suitable for general laboratories.

Furthermore, after purification, the product is filtered several times and then is crystallized to remove impurities. Yet the solvent is N,N-dimethylformamide (DMF) with high boiling point and the coupling agents including N,N'-dicyclohexyl-carbodiimide (DCC) and N-Hydroxybenzotrizole (HOBt). These are all difficult to be removed completely by filtering or recrystallization. This causes troubles to the next process.

SUMMARY OF THE INVENTION

Therefore it is a primary object of the present invention to provide a method for preparing a precursor that is used for labeling hepatocyte receptors and containing trisaccharide and DTPA ligand in which C18 reversed phase columns (RP-18 column) are used to purify products having trisaccharide structure and silica gel columns are used for purification during synthesis of single-chain Gal-NAc (N-acetylgalactosamine). Thus purification times and cost associated with each purification process are reduced. Therefore the time and cost are saved.

It is another object of the present invention to provide a method for preparing a precursor that is used for labeling hepatocyte receptors and containing trisaccharide and DTPA ligand in which boron trifluoride diethyl etherate (BF$_3$—OEt$_2$) is used as a catalyst in a glycosylation reaction to simplify the synthesis process.

It is a further object of the present invention to provide a method for preparing a precursor that is used for labeling hepatocyte receptors and containing trisaccharide and DTPA ligand in which diethyl ether is used to facilitate precipitation of products and remove a part of coupling reagent. Removing the coupling reagent is good for purification of products.

It is a further object of the present invention to provide a method for preparing a precursor that is used for labeling hepatocyte receptors and containing trisaccharide and DTPA ligand in which $N^\alpha,N^\alpha$-bis(carboxymethyl)-L-lysine hydrate and benzyl chloroformate are coupled to form a trisaccharide skeleton. Thus it is ensured that the following synthesis and yield rate of trisaccharide are not affected by a factor that only one carboxyl acid is connected.

It is a further object of the present invention to provide a method for preparing a precursor that is used for labeling hepatocyte receptors and containing trisaccharide and DTPA ligand. The DTPA ligand of the precursor prepared can bond to radioactive isotopes or magnetic metal. Together with the affinity of trisaccharide to liver cells, the precursor is a bifunctional compound. The special structure of the precursor helps the precursor stay on surfaces of liver cells and the precursor is suitable to produce radiotracers for liver-related imaging.

In order to achieve the above objects, a method for preparing a precursor that is used for labeling hepatocyte receptors and containing trisaccharide and DTPA ligand according to the present invention includes following steps: (1) coupling 6-aminohexanol (ah) to N-Carbobenzyloxyglycine (Z-G), generate an amide bond and form a compound Z-G-ah; (2)

joining Z-G-ah with GalNAc(OAc)₄ in a solvent with a catalyst; the catalyst is boron trifluoride etherate; (3) removing an acetyl protecting group by using sodium methoxide to get a compound Z-G-ah-GalNAc, then use a silica gel column for separation and purification; (4) hydrogenizing the compound Z-G-ah-GalNAc to remove carboxybenzyl and obtain a compound G-ah-GalNAc; (5) coupling $N^\alpha,N^\alpha$-bis(carboxymethyl)-L-lysine hydrate to benzyl chloroformate and get a compound Z-DCM-Lys (ε-benzyloxycarbonyl-α-dicarboxylmethyl-L-lysine); (6) coupling the compound G-ah-GalNAc to the compound Z-DCM-Lys, generate an amide bond and get a compound Z-DCM-Lys(G-ah-GalNAc)₃; then add diethyl ether to make the compound Z-DCM-Lys(G-ah-GalNAc)₃ precipitate out and purify the compound by a liquid chromatographic column; (7) hydrogenizing the compound Z-DCM-Lys(G-ah-GalNAc)₃ to remove carboxybenzyl and get a compound DCM-Lys(G-ah-GalNAc)₃; (8) coupling the compound DCM-Lys(G-ah-GalNAc)₃ to N-Benzyloxycarbonyl-6-aminohexanoic acid (Z-aha) and then hydrogenize again for removing carboxybenzyl to get a compound aha-DCM-Lys(G-ah-GalNAc)₃; and (9) coupling the compound aha-DCM-Lys(G-ah-GalNAc)₃ to a DTPA-dianhydride and get a compound DTPA-aha-DCM-Lys(G-ah-GalNAc)₃; next use a liquid chromatographic column for separation and purification of the compound. The final product DTPA-aha-DCM-Lys(G-ah-GalNAc)₃ is a precursor used for labeling hepatocyte receptors and containing trisaccharide and DTPA ligand.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

In order to overcome shortcomings of conventional method of manufacturing hepatocyte receptor labeled precursors such as high cost, not suitable for general laboratories, or inconvenience, a new method according to the present invention is provided.

Figure 1:
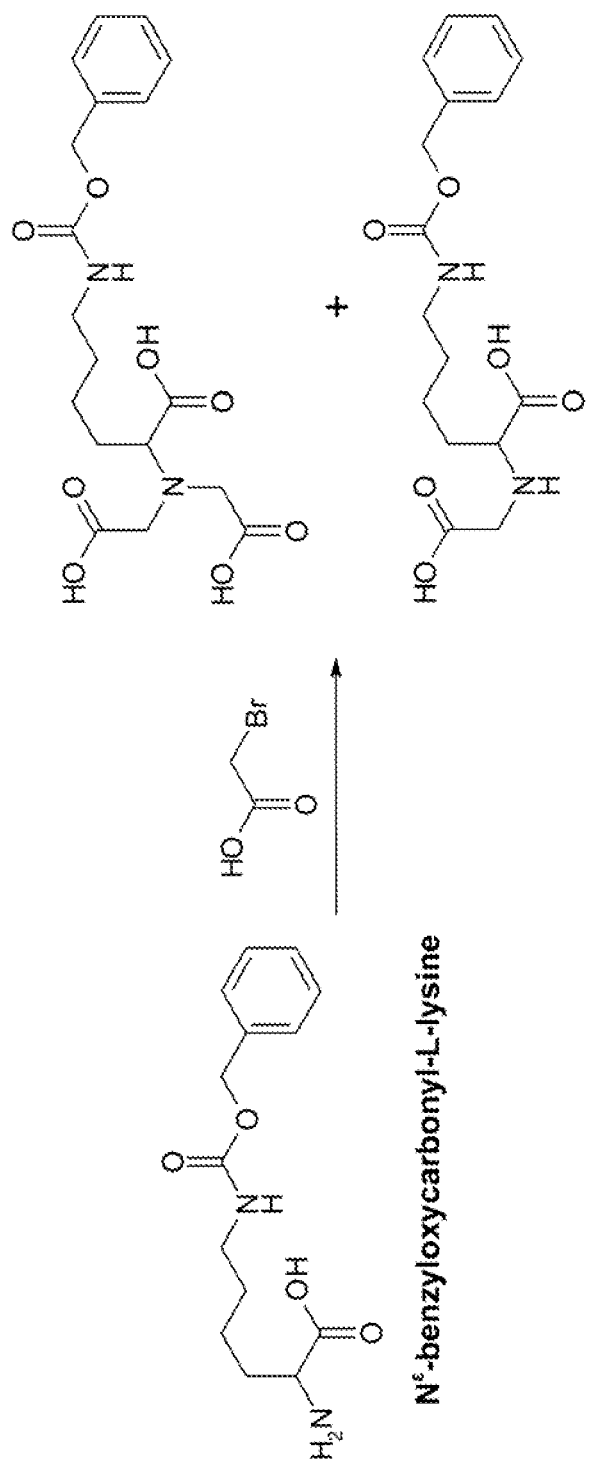
FIG. 1 is a schematic diagram showing the synthesis of trisaccharide skeleton of a prior art.
Figure 2:
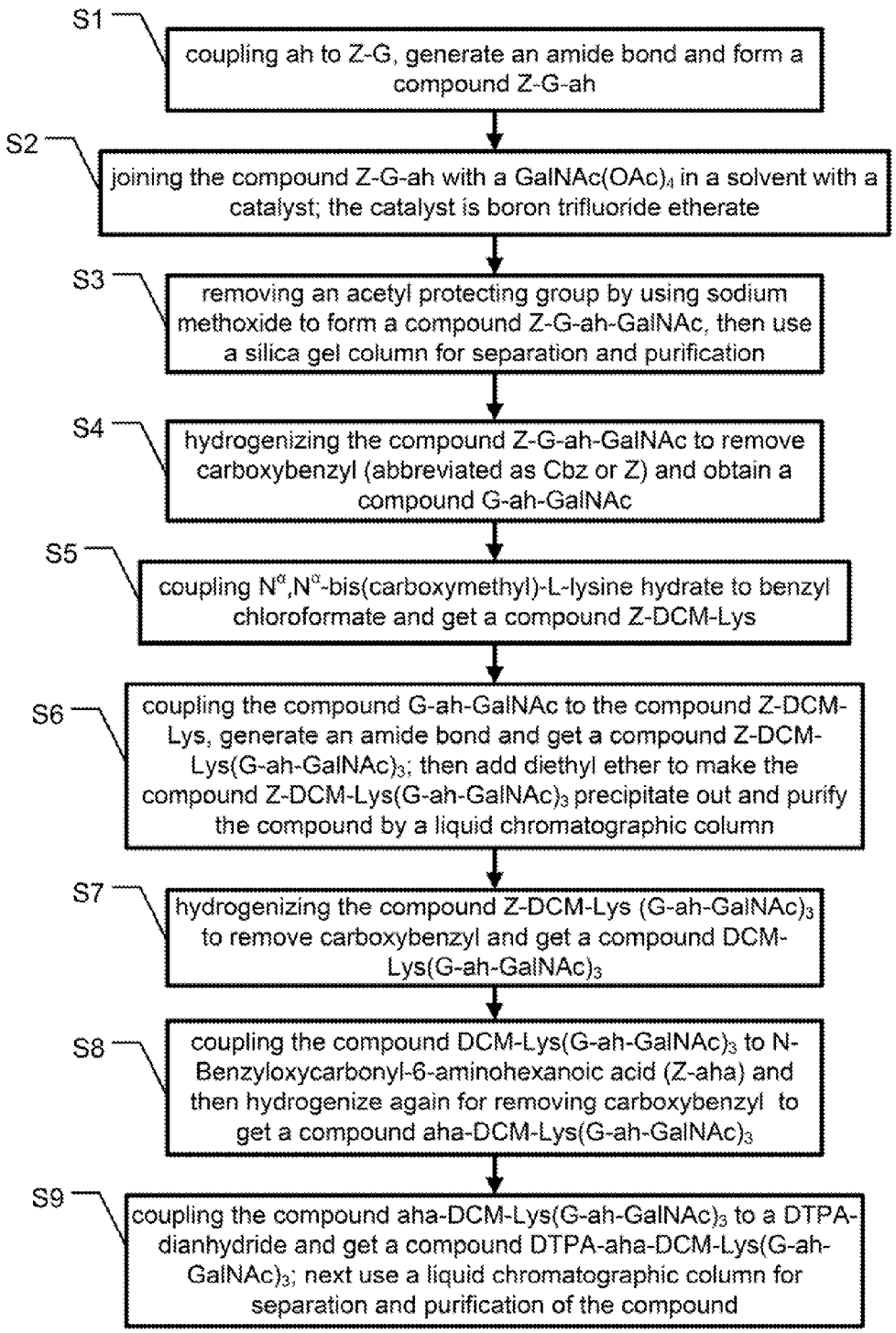
FIG. 2 is a flow chart showing steps of preparing a precursor used for labeling hepatocyte receptors and containing trisaccharide and DTPA ligand of an embodiment according to the present invention.

Refer to FIG. 2, a method for preparing a precursor that is used for labeling hepatocyte receptors and containing trisaccharide and DTPA ligand of the present invention includes following steps:

Step S1: coupling ah to Z-G, generate an amide bond and form a compound Z-G-ah;

Step S2: joining the compound Z-G-ah with a GalNAc(OAc)₄ in a solvent with a catalyst; the catalyst is boron trifluoride etherate.

Step S3: removing an acetyl protecting group by using sodium methoxide to form a compound Z-G-ah-GalNAc, then use a silica gel column for separation and purification;

Step S4: hydrogenizing the compound Z-G-ah-GalNAc to remove carboxybenzyl (abbreviated as Cbz or Z) and obtain a compound G-ah-GalNAc;

Step S5: coupling $N^\alpha,N^\alpha$-bis(carboxymethyl)-L-lysine hydrate to benzyl chloroformate and get a compound Z-DCM-Lys;

Step S6: coupling the G-ah-GalNAc to the compound Z-DCM-Lys, generate an amide bond and get a compound Z-DCM-Lys(G-ah-GalNAc)₃; then add diethyl ether to make the compound Z-DCM-Lys(G-ah-GalNAc)₃ precipitate out and purify the compound by a liquid chromatographic column;

Step S7: hydrogenizing the compound Z-DCM-Lys (G-ah-GalNAc)₃ to remove carboxybenzyl and get a compound DCM-Lys(G-ah-GalNAc)₃;

Step S8: coupling the compound DCM-Lys(G-ah-GalNAc)₃ to N-Benzyloxycarbonyl-6-aminohexanoic acid (Z-aha) and then hydrogenize again for removing carboxybenzyl to get a compound aha-DCM-Lys(G-ah-GalNAc)₃:

Step S9: coupling the compound aha-DCM-Lys(G-ah-GalNAc)₃ to a DTPA-dianhydride and get a compound DTPA-aha-DCM-Lys(G-ah-GalNAc)₃; next use a liquid chromatographic column for separation and purification of the compound.

Figure 3:
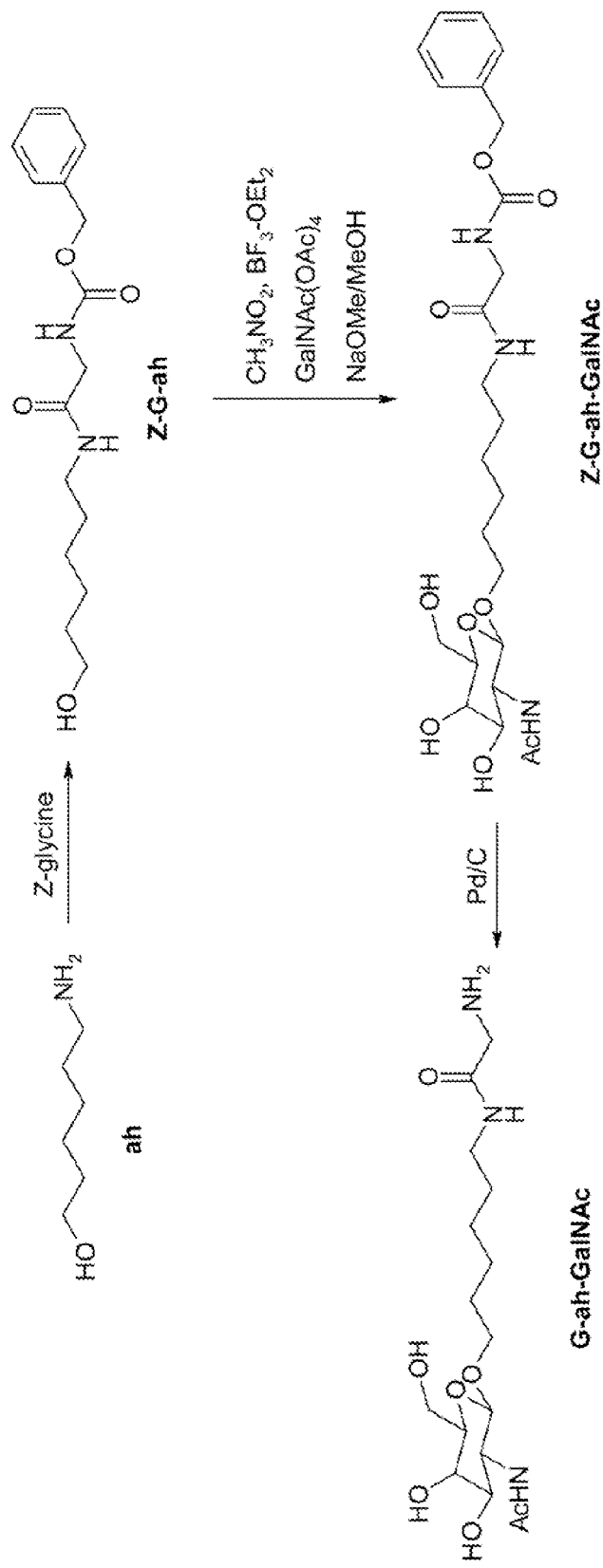
FIG. 3 is a schematic diagram showing the synthesis of G-ah-GalNAc of an embodiment according to the present invention.

In the step S1 to step S4, the synthesis process of G-ah-GalNAc, refer to FIG. 3, firstly couple 6-aminohexanol (ah) to Z-glycine (carboxybenzyl glycine) and an amide bond is generated therebetween to form a compound Z-G-ah. The carboxybenzyl is used as a protecting group for amino groups. Although there are several kinds of protecting groups for amino groups, which one is optimal depends on the use of the compound. By considering the following reactions, carboxybenzyl is used because it is easy to be released during hydrogenation reaction and it has no effect on other functional groups of the molecule.

Then dissolve the compound Z-G-ah in a solvent and add a catalyst so as to join Z-G-ah with GalNAc(OAc)₄ by glycosylation. The solvent can be anhydrous nitromethane or dichloromethane. The catalyst can be boron trifluoride diethyl etherate (BF₃—OEt₂) or trimethylsililyl trifluoromethanesulfonate (TMSOTf). Next de-acetylation is performed by using sodium methoxide to get a compound.

After formation of Z-G-ah-GalNAc, the next step is purification of Z-G-ah-GalNAc. The method used now is by a silica gel column and elution with organic solvents, done at once. The organic solvents include dichloromethane and methanol. There is no need to use hydroxide ion exchange resin. Moreover, the silica gel column is low-cost, thus the separation and purification can be achieved without high expenditures.

After purification, a catalytic hydrogenation/reduction using a palladium carbon (Pd/C) catalyst is performed to remove carboxybenzyl and get the compound G-ah-GalNAc.

During the hydrogenation/reduction reaction, carboxybenzyl is released easily without influence on other functional groups of the molecule. After the reaction being completed, pure product is obtained only by simple filtering and no other purification process is required. The processing after deprotection reaction is simple and the high cost of materials for purification is also saved.

Figure 4:
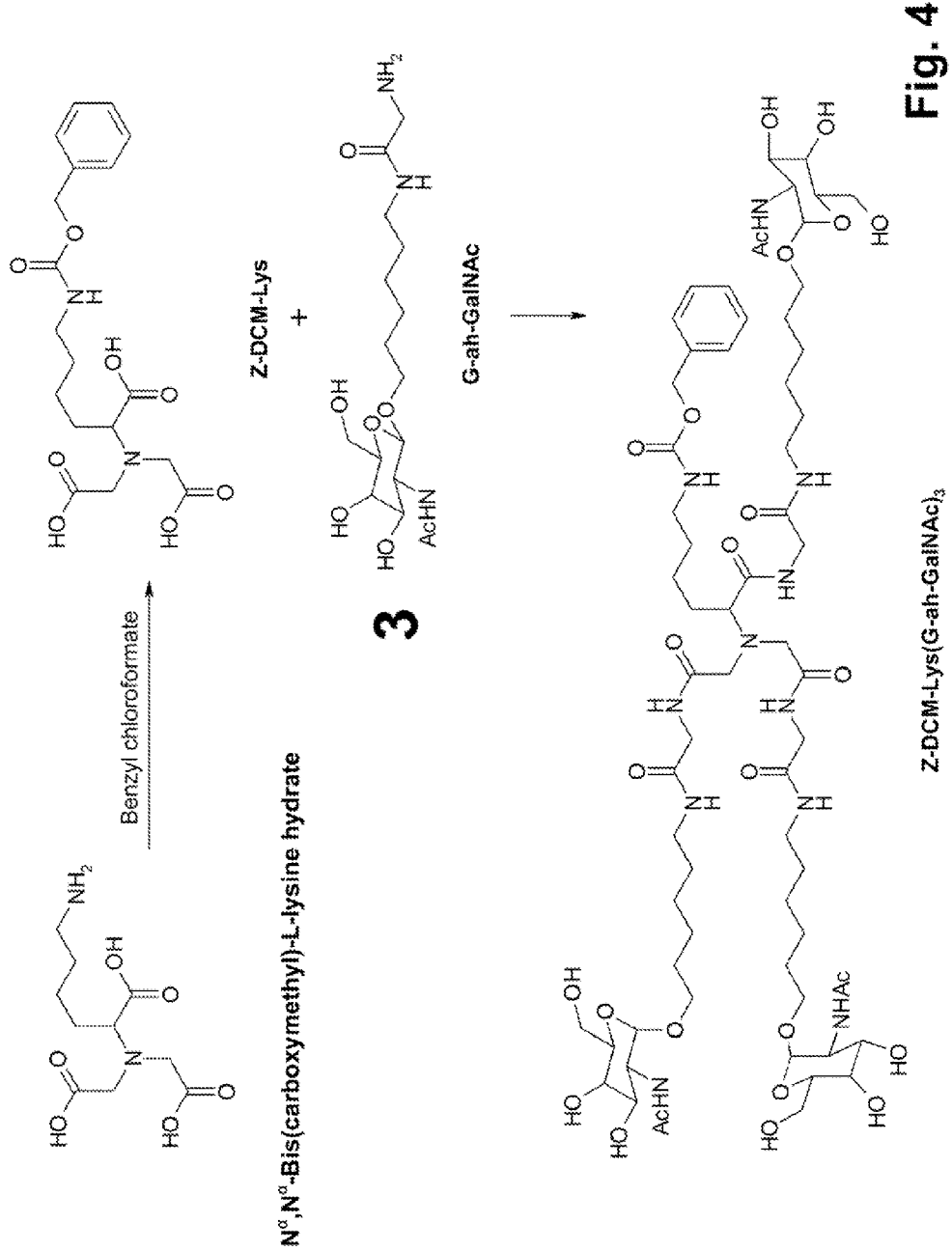
FIG. 4 is a schematic diagram showing the synthesis of Z-DCM-Lys(G-ah-GalNAc)₃ of an embodiment according to the present invention.

As to the step S5, refer to FIG. 4, $N^\alpha,N^\alpha$-bis(carboxymethyl)-L-lysine hydrate is used as a skeleton of trisaccharide in the present invention. $N^\alpha,N^\alpha$-bis(carboxymethyl)-L-lysine hydrate is coupled to benzyl chloroformate to get a compound Z-DCM-Lys. By using these compounds as reactants, the problem of the skeleton only connected with one carboxyl acid can be avoided. If there is only one carboxyl acid connected to the skeleton, the trisaccharide structure is not formed during following reaction with G-ah-GalNAc. Thus the yield rate is reduced and there is an additional step of separating side products.

In the step S6 and step S7, amide bonds form between those G-ah-GalNAc and Z-DCM-Lys. Still refer to FIG. 4, Z-DCM-Lys(G-ah-GalNAc)$_3$ is obtained. Then remove Z protecting group by hydrogenation to get DCM-Lys(G-ah-GalNAc)$_3$.

In the step S6, the amide bond is generated by dissolving G-ah-GalNAc and Z-DCM-Lys in anhydrous DMF and then adding N-Hydroxybenzotrizole (HOBt), and N,N-Diisopropylethylamine (DIEA) into the solution in turn. The solution temperature is decreased into 0 degree Celsius (□) and is added with 1-(3-Dimethylaminopropyl)-3-ethylcarbodiimide (EDCI).

In order to purify and separate out the product, diethyl ether is used in the present invention to facilitate precipitation of the product. The precipitation is further purified. The purification way is different from the silica gel column used in the step S3. A C18 reverse phase (RP-18) column for liquid chromatography is used. The method is simple and the effect is good. The products with high purity can be obtained by the column at one time and the column is reusable. Thus the cost is down. The purification way is suitable for compounds containing trisaccharide.

The purified products are dried by a freeze dryer. After being dried and separated, the distribution of the products in the tube is easy to be observed.

Figure 5:
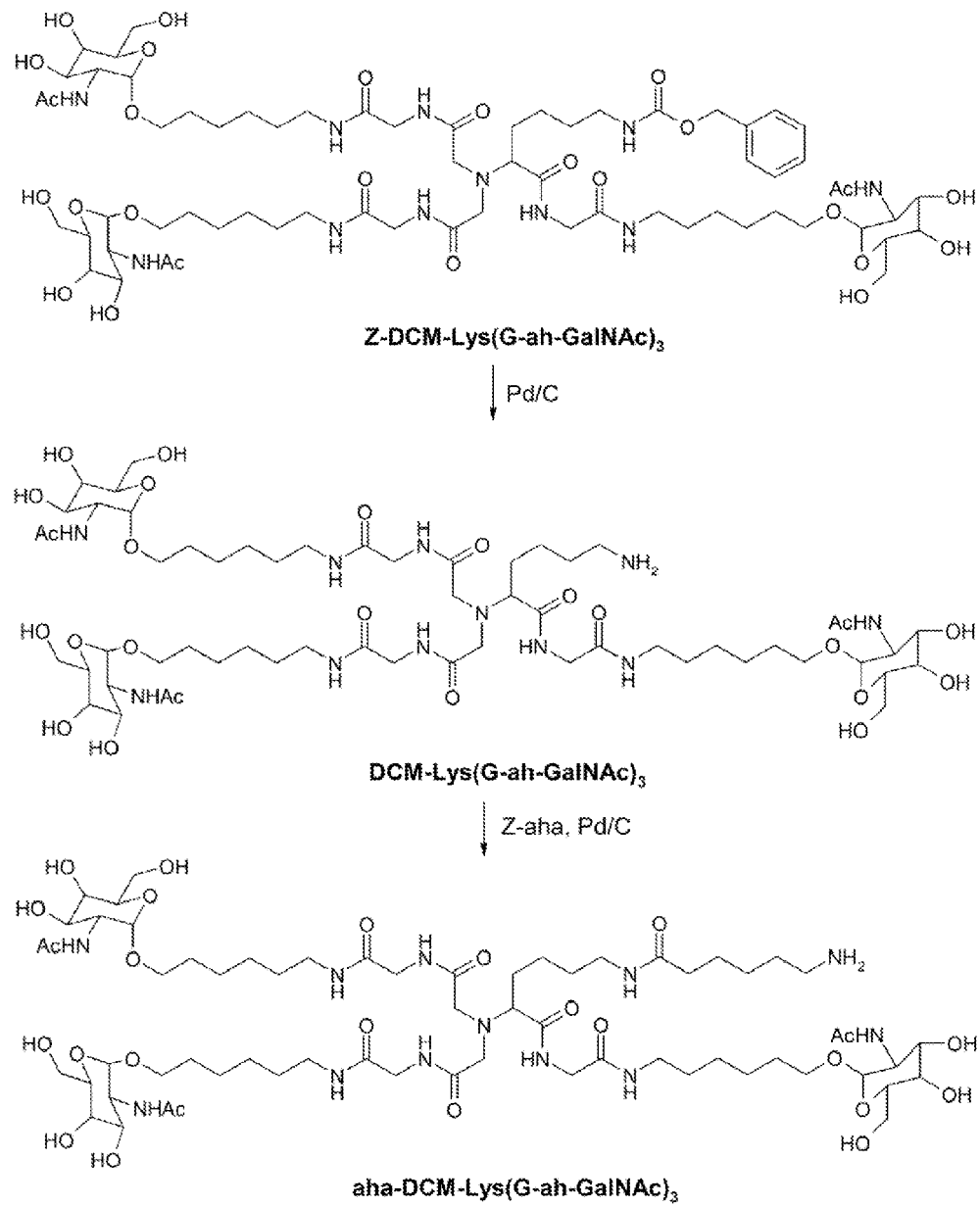
FIG. 5 is a schematic diagram showing the synthesis of aha-DCM-Lys(G-ah-GalNAc)₃ of an embodiment according to the present invention.

Refer to FIG. 5, the step S8 is a previous step designed for coupling the above compound to DTPA structure. The purpose of connection with DTPA is in that the final products of the present invention have high affinity to hepatocyte due to carbohydrate (saccharide) substrate of DTPA. Moreover, they can also bond with radioactive isotopes to provide radiolabeling services. In this step, the compound DCM-Lys(G-ah-GalNAc)$_3$ is coupled to N-Benzyloxycarbonyl-6-aminohexanoic acid (Z-aha). The amino group of Z-aha is also protected by carboxybenzyl which is easily released without effect on other functional groups of the molecule. After hydrogenation and carboxybenzyl being removed, a compound aha-DCM-Lys(G-ah-GalNAc)$_3$ is obtained.

Figure 6:
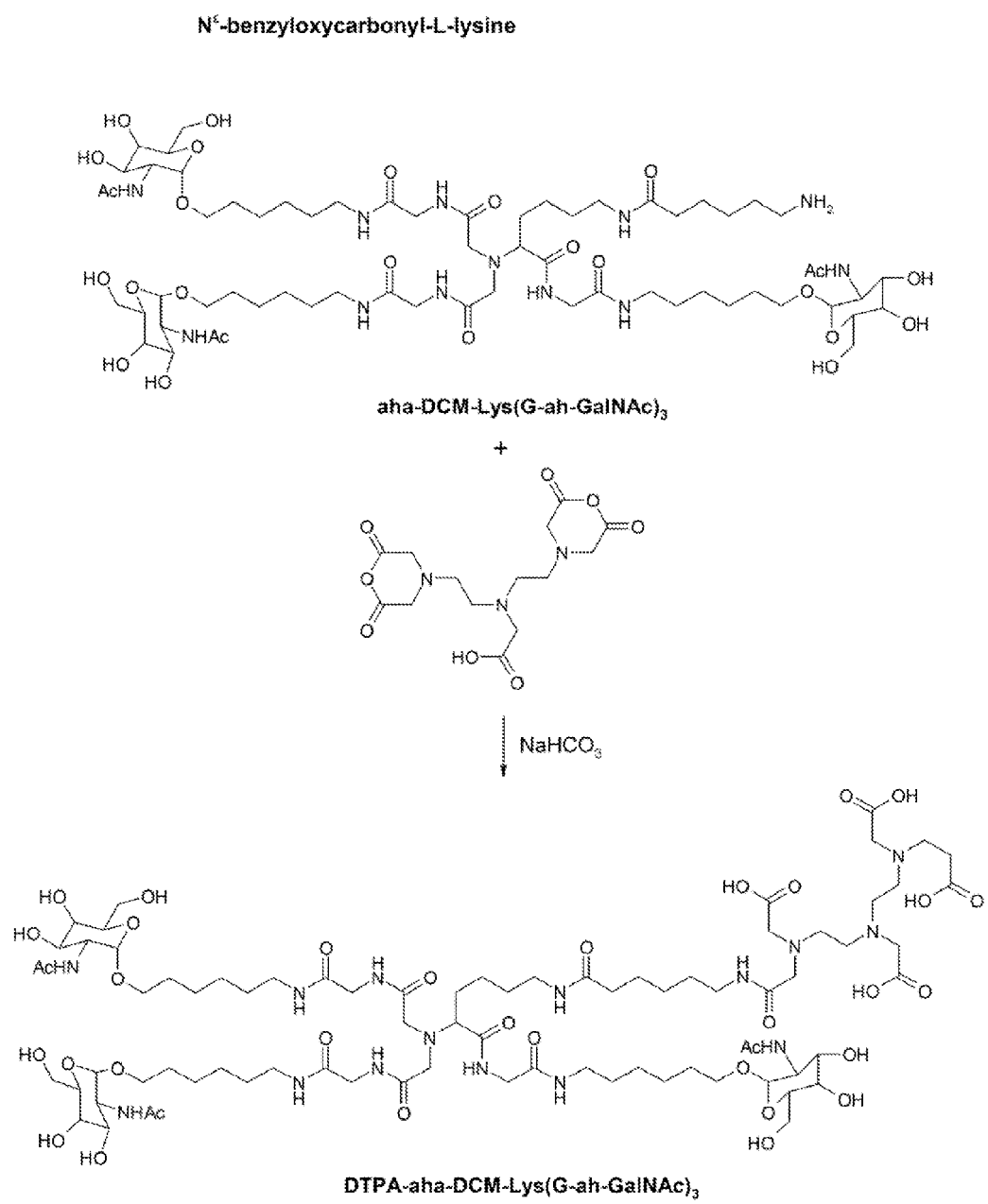
FIG. 6 is a schematic diagram showing the synthesis of DTPA-aha-DCM-Lys(G-ah-GalNAc)₃ of an embodiment according to the present invention.

Refer to FIG. 6, the last step S9 is shown. As shown in figure, aha-DCM-Lys(G-ah-GalNAc)$_3$ and DTPA-dianhydride are coupled in a solvent. The solvenet is saturated sodium bicarbonate aqueous solution. Finally, DTPA-aha-DCM-Lys (G-ah-GalNAc)$_3$ containing trisaccharide and DTPA ligand and used as a precursor for labeling hepatocyte receptors is obtained.

The product DTPA-aha-DCM-Lys(G-ah-GalNAc)$_3$ contains trisaccharide structure. Thus the RP-18 column for liquid chromatography is used. The purified product is dried by a freezer dryer. After being dried and separated, the product distribution in the tube is easy to be observed. No complicated test methods are required. For example, TPTZ analysis is complicated and time-consuming.

In the present invention, during the synthesis process of single-chain N-acetylgalactosamine, Z-G-ah-GalNAc, carboxybenzyl is used as a protecting group for convenience of work flow. And the key point is in that when the respective product needs to be purified, there is no need to use Sephadex gel chromatography with high cost and acetic acid solution for elution. The silica gel column is used for purification during the synthesis process of the single-chain N-acetylgalactosamine, Z-G-ah-GalNAc. Moreover, the RP-18 column for liquid chromatography is used to purify compounds that contain trisaccharide. Thus not only the number of purification times is reduced, the cost of each purification process is down. And the use of diethyl ether that facilitates precipitation of products with trisaccharide also makes purification more convenient.

The final product of the present invention DTPA-aha-DCM-Lys(G-ah-GalNAc)$_3$ containing trisaccharide and DTPA ligand can further bond to a radioactive isotope by the DTPA structure so as to form a radiotracer of the precursor used for labeling hepatocyte receptors and containing trisaccharide and DTPA ligand. The radioactive isotope can be $^{99m}$Tc, $^{68}$Ga or $^{111}$In, used for radiolabeling. Or DTPA-aha-DCM-Lys(G-ah-GalNAc)$_3$ containing trisaccharide and DTPA ligand is bound to a magnetic metal such as a gadolinium ion or a metal ion belong to iron group elements, and then is applied to magnetic resonance imaging contrast agents.

Besides the DTPA ligand that can bond to radioactive isotopes, the final product of the present invention also includes a trisaccharide structure. The trisaccharide structure has high affinity and specificity to ASGPR and this helps targeting of the final product of the present invention to liver cells. Based on excellent targeting effect, the final product of the present invention is good raw material for radiotracers used to label liver cells. Thus radioactive labeling of the liver cells is attained.

It is proved that DTPA-aha-DCM-Lys(G-ah-GalNAc)$_3$ do have a high application value. The method of the present invention is suitable for general laboratories due to convenience and low-cost.

The followings are details and related parameters of each step according to the present invention.

Synthesis of Z-G-ah

Benzyl(6-hydroxyhexylcarbamoyl)methylcarbamate

Put 6-aminohexanol (ah) (1.5 g, 12.82 mmole), Z-glycine (2.2 g, 10.68 mmole), and 4 Å molecular sieve into a 100 ml round-bottom flask and run a pump to create vacuum for 2 hours. Then dissolve in 25 ml anhydrous DMF and stir at room temperature for 5 minutes (min). Next add anhydrous N-Hydroxybenzotrizole (HOBt) (1.72 g, 12.82 mmole), and N,N-Diisopropylethylamine (DIEA) (2.23 mL, 12.82 mmole) into the solution in turn and the solution temperature is decreased into 0□. After being added with 1-(3-Dimethylaminopropyl)-3-ethylcarbodiimide (EDCI) (2.45 g, 12.82 mmole), the solution is stirred at room temperature overnight. The suspension is filtered and diluted with dichloromethane solution. Then use 1N HCl, saturated sodium bicarbonate (NaHCO$_3$), water and Brine (50 mL) in turn for extraction. After being washed, the dichloromethane solution is dried by anhydrous sodium sulfate and then filter and dry in vacuum to get white solid product Z-G-ah (2.29 g, 7.5 mmole). The yield rate is 70%.

Compound Data of the Product (Including FT-IR Data, NMR Data, and ESI-MS Data):

IR (KBr) 3386 and 3265 (NH), 2918 (CH$_2$), 1690 and 1650 (CO) cm$^{-1}$.

$^1$H-NMR (CD$_3$OD, 300 MHz): 7.40 (m, 5H), 5.10 (s, 2H), 3.73 (d, 2H), 3.53 (t, 2H), 3.18 (t, 2H), 1.50 (m, 4H), 1.36 (m, 4H).

$^{13}$C-NMR (CD$_3$OD, 75 MHz): 170.92, 157.85, 136.93, 128.30, 127.88, 127.76, 66.67, 61.69, 43.76, 39.15, 32.36, 29.22, 26.54, 25.43.

ESI-MS: m/z 331.20 (M+Na)$^+$.

Synthesis of Z-G-ah-GalNAc 6-carboxybenzyl-glycyl-aminohexyl-β-GalNAc

Dissolve compound GalNAc(OAc)$_4$ (1 g, 2.57 mmole) and compound Z-G-ah (940 mg, 3.05 mmole) in 20 mL nitromethane (CH$_3$NO$_2$) and the solution temperature is cooled to 0□. Slowly add drops of Boron trifluoride diethyl etherate (BF$_3$—OEt$_2$) (0.65 mL, 5.14 mmole) into the solution and stir the solution for 30 min. Then react at room temperature for 3 days. Add dichloromethane solution used for dilution. Next use saturated sodium bicarbonate (NaHCO$_3$) and Brine (50 mL) in turn for extraction. After being washed, the dichloromethane solution is dried by anhydrous sodium sulfate and the filter and dry in vacuum to get 1.43 g crude product. Dissolve the crude product in 40 mL methanol and then add 1M NaOMe/MeOH solution (7.36 mL). Stir the solution overnight. Add Dowex 50W X8 (H$^+$ form) for neutralization. After being filtered, the solution is concentrated. Next use liquid chromatography (SiO$_2$, CH$_2$Cl$_2$:CH$_3$OH=4:1) for separation and purification to get white solid product Z-G-ah-GalNAc (920 mg, 1.79 mmole). The yield rate is 65-75%.

Compound Data of the Product:

IR (KBr) 3392 and 3266 (NH), 2921 (CH$_2$), 1691 and 1651 (CO) cm$^{-1}$.

$^1$H-NMR (CD$_3$OD, 300 MHz): 7.40-7.24 (m, 5H), 5.09 (s, 2H), 4.37 (d, 1H), 3.98-3.82 (m, 3H), 3.80-3.67 (m, 4H$_2$), 3.64-3.58 (dd, 1H), 3.56-3.41 (t, 2H), 3.17 (t, 2H), 1.96 (s, 3H), 1.60-1.42 (m, 4H), 1.40-1.23 (m, 4H).

$^{13}$C-NMR (CD$_3$OD, 75 MHz): 172.80, 170.91, 157.85, 136.94, 128.30, 127.88, 127.74, 101.87, 75.48, 72.12, 69.12, 68.48, 66.65, 61.32, 53.16, 43.75, 39.13, 29.31, 29.19, 26.37, 25.56, 21.89.

ESI-MS: m/z 512.19 (M+H)$^+$, 534.26 (M+Na)$^+$.

Synthesis of G-ah-GalNAc

6-Glycylaminohexyl-β-GalNAc

Dissolve Z-G-ah-GalNAc (640 mg, 1.25 mmole) into 80% methanol and add 10% Pd/C catalyst (90 mg) into the solution. Put the solution into a reduction device and vibrate the solution in 50 psi hydrogen gas. After about 17 hours, filter the solution and dry the filtrate under reduced pressure to get the compound G-ah-GalNAc (0.47 g, 1.24 mmole). The yield rate is 99%.

Compound Data of the Product:

IR (KBr) 3387 and 3266 (NH), 2921 (CH$_2$), 1654 (CO) cm$^{-1}$.

$^1$H NMR (CD$_3$OD, 300 MHz): 4.34 (d, 1H), 3.99-3.83 (m, 3H), 3.80-3.67 (d, 2H), 3.64-3.54 (dd, 1H), 3.53-3.41 (t, 2H), 3.34 (s, 2H), 3.21 (t, 2H), 1.96 (s, 3H), 1.60-1.42 (m, 4H), 1.43-1.25 (m, 4H).

$^{13}$C-NMR (CD$_3$OD, 75 MHz): 172.80, 171.29, 101.96, 75.44, 72.04, 69.25, 68.48, 61.32, 53.08, 42.73, 39.15, 29.34, 29.17, 26.49, 25.64, 21.93.

ESI-MS: m/z 378.38 (M+H)$^+$.

Synthesis of Z-DCM-Lys

N$^\alpha$-benzyloxycarbonyl-N$^\alpha$-dicarboxymethyl-L-lysine

Dissolve N$^\alpha$,N$^\alpha$-Bis(carboxymethyl)-L-lysine hydrate (5 g, 0.019 mole) in saturated sodium bicarbonate aqueous solution (20 ml) and then is cooled in an ice bath. Take and dissolve benzyl chloroformate (3.4 ml, 0.0229 mole) in diethyl ether (20 ml) and then is slowly dropped into the above solution by an addition funnel. Then stir the solution at room temperature for 4 hours. Take aqueous phase of the solution and use diethyl ether for extraction (50 ml, 3 times). Take the aqueous phase and adjust the pH value to 2 by using concentrated hydrochloric acid, and cause some solid precipitated out. Filter and get the solid to obtain white solid product Z-DCM-Lys (5.9 g, 0.015 mole). The yield rate is 78%.

Compound Data of the Product:

$^1$H NMR (DMSO, 300 MHz): δ 7.36-7.20 (m, 5H), 4.98 (s, 2H), 3.41-3.20 (m, 5H), 2.92 (t, 2H), 1.58-1.24 (m, 6H).

ESI-MS: m/z 397.19 (M+H)$^+$ and 419.18 (M+Na)$^+$.

Synthesis of Z-DCM-Lys(G-ah-GalNAc)$_3$

N$^\alpha$-benzyloxycarbonyl-N$^\alpha$-dicarboxylmethyl-L-lysine-tris(glycylaminohexyl-N-acetylgalactosamine)

Put compound G-ah-GalNAc (457 mg, 1.21 mmole) and compound Z-DCM-Lys (120 mg, 0.303 mmol) into a 100 mL round-bottom flask and run a pump to create vacuum for 2 hours. Then dissolve in 15 ml anhydrous DMF and stir at room temperature for 5 min. Next add anhydrous N-Hydroxybenzotrizole (HOBt) (155.5 mg, 1.15 mmole), and N,N-Diisopropylethylamine (DIEA) (0.4 mL, 2.3 mmole) into the solution in turn and the solution temperature is cooled to 0□. After being added with 1-(3-Dimethylaminopropyl)-3-ethylcarbodiimide (EDCI) (220 mg, 1.15 mmole), the solution is stirred at room temperature overnight. Add diethyl ether to make the product precipitate and then remove the diethyl ether layer and dry the solution in vacuum. Next use liquid chromatography (RP-18, 30% MeOH-55% MeOH with 1% TEA) for separation and use a freezer dryer for drying. Thus white solid product Z-DCM-Lys(G-ah-GalNAc)$_3$ (340 mg, 0.23 mmol) is obtained. The yield rate is 76%.

Compound Data of the Product:

IR (KBr) 3410 and 3196 (NH), 2921 (CH$_2$), 1654 (CO) cm$^{-1}$.

$^1$H NMR (D$_2$O, 300 MHz): δ 7.36-7.20 (m, 5H), 4.96 (s, 2H), 4.37-4.21 (d, 3H), 3.81-2.95 (m, 43H), 1.95 (s, 9H), 1.60-1.01 (m, 30H).

$^{13}$C NMR (D$_2$O, 75 MHz): δ 175.24, 174.63, 170.97, 158.48, 136.94, 128.93, 128.47, 127.75, 101.76, 75.20, 71.19, 70.37, 67.95, 66.80, 61.08, 55.68, 52.62, 42.44, 40.24, 39.55, 28.68, 28.55, 25.87, 24.91, 22.76, 22.43.

ESI-MS: m/z 738.46 (M+2H)$^{+2}$ and 1474.65 (M+H)$^+$.

Synthesis of DCM-Lys(G-ah-GalNAc)$_3$

N$^\alpha$-dicarboxylmethyl-L-lysine-tris(glycylaminohexyl-N-acetylgalactosamine)

The synthesis method is the same as the method for synthesis of G-ah-GalNAc. Take compound Z-DCM-Lys(G-ah-GalNAc)$_3$ (340 mg, 0.23 mmol) and then perform hydrogenation/reduction reaction to get white compound DCM-Lys(G-ah-GalNAc)$_3$ (296 mg, 0.22 mmol). The yield rate is 96%.

Compound Data of the Product:

IR (KBr) 3410 and 3196 (NH), 2921 (CH$_2$), 1654 (CO) cm$^{-1}$.

$^1$H NMR (D$_2$O, 300 MHz): δ 4.35-4.21 (d, 3H), 3.81-2.62 (m, 43H), 1.86 (s, 9H), 1.60-1.01 (m, 30H).

$^{13}$C NMR (D$_2$O, 75 MHz): δ 175.16, 174.52, 171.01, 101.76, 75.20, 71.17, 70.39, 67.94, 65.30, 61.09, 55.66, 52.60, 42.44, 39.70, 39.56, 28.67, 28.53, 25.84, 24.91, 22.81, 22.42.

ESI-MS: m/z 671.10 (M+2H)$^{+2}$ and 1340.69 (M+H)$^+$.

Synthesis of Z-aha-DCM-Lys(G-ah-GalNAc)₃

N^α-benzyloxycarbonyl-6-aminohexanoyl-N^α-dicarboxylmethyl-L-lysine-tris(glycylaminohexyl-N-acetylgalactosamine)

Put compound DCM-Lys(G-ah-GalNAc)₃ (167 mg, 0.124 mmole) and compound Z-aha (31 mg, 0.117 mmol) into a 100 mL round-bottom flask and run a pump to create vacuum for 2 hours. Then dissolve in 10 ml anhydrous DMF and stir at room temperature for 5 min. Next add anhydrous HOBt (16.8 mg, 0.124 mmole), and DIEA (40.67 µL, 0.24 mmole) into the solution in turn and the solution temperature is cooled to 0☐. Then add EDCI (24 mg, 0.124 mmole) into the solution and stir the solution at room temperature overnight. Dry DMF in vacuum and then use liquid chromatography (RP-18, 30% MeOH-55% MeOH with 1% TEA) for separation and purification. Next use a freezer dryer for drying. Thus white solid product Z-aha-DCM-Lys(G-ah-GalNAc)₃ (133 mg, 0.084 mmol) is obtained. The yield rate is 72%.

Compound Data of the Product:

IR (KBr) 3410 and 3196 (NH), 2921 ($CH_2$), 1654 (CO) $cm^{-1}$.

$^1$H NMR ($D_2O$, 300 MHz): δ 7.36-7.20 (m, 5H), 4.92 (s, 2H), 4.37-4.21 (d, 3H), 3.81-2.95 (m, 43H), 2.80-2.75 (t, 2H), 2.20-2.00 (t, 2H), 1.95 (s, 9H), 1.60-1.01 (m, 36H).

$^{13}$C NMR ($D_2O$, 75 MHz): δ 176.65, 175.09, 174.61, 170.94, 158.44, 136.71, 128.91, 128.46, 127.72, 101.76, 75.20, 71.19, 70.35, 67.95, 66.76, 65.27, 61.08, 55.69, 52.61, 42.43, 42.32, 40.41, 39.57, 39.05, 35.80, 28.69, 28.57, 28.31, 28.02, 25.89, 25.44, 25.23, 24.93, 23.05, 22.43.

ESI-MS: m/z 794.96 $(M+2H)^{+2}$ and 1588.59 $(M+H)^+$.

Synthesis of aha-DCM-Lys(G-ah-GalNAc)₃

6-aminohexanoyl-N^α-dicarboxylmethyl-L-lysine-tris(glycylaminohexyl-N-acetylgalactosamine)

The method is the same as the method for synthesis of G-ah-GalNAc. Take compound
Z-aha-DCM-Lys(G-ah-GalNAc)₃ (110 mg, 0.069 mmol) and perform hydrogenation/reduction reaction to get white compound aha-DCM-Lys(G-ah-GalNAc)₃ (100 mg, 0.068 mmol). The yield rate is 99%.

Compound Data of the Product:

IR (KBr) 3410 and 3196 (NH), 2921 ($CH_2$), 1654 (CO) $cm^{-1}$.

$^1$H NMR ($D_2O$, 300 MHz): δ 4.37-4.21 (d, 3H), 3.90-2.90 (m, 43H), 2.89-2.70 (t, 2H), 2.20-2.00 (t, 2H), 1.95 (s, 9H), 1.65-1.05 (m, 36H).

$^{13}$C NMR ($D_2O$, 75 MHz): δ 176.60, 175.23, 174.65, 171.03, 101.80, 75.23, 71.21, 70.39, 67.99, 65.27, 61.12, 55.73, 52.63, 42.49, 39.59, 39.14, 35.73, 28.72, 28.58, 28.31, 28.08, 25.89, 25.40, 25.15, 24.95, 23.04, 22.47.

ESI-MS: m/z 727.78 $(M+2H)^{+2}$ and 1453.88 $(M+H)^+$.

Synthesis of DTPA-aha-DCM-Lys(G-ah-GalNAc)₃

Take and put compound aha-DCM-Lys(G-ah-GalNAc)₃ (70 mg, 0.048 mmol) into a sample container and then add DTPA-bis(anhydride)(104 mg, 0.29 mmol) into the sample container. This compound is available. Stir the solution at room temperature for 30 min. Again add DTPA-bis(anhydride) (70 mg) into the solution and stir the solution at room temperature for 1 hour. Then use liquid chromatography (RP-18, 10% MeOH-60% MeOH in 50 mM amino acetate) for separation and purification. Next use a freezer dryer for drying. Finally white solid product DTPA-aha-DCM-Lys(G-ah-GalNAc)₃ (62 mg, 70%) is obtained.

Compound Data of the Product:

IR (KBr) 3410 and 3196 (NH), 2921 ($CH_2$), 1654 (CO) $cm^{-1}$.

$^1$H NMR ($D_2O$, 300 MHz): δ 4.37-4.25 (d, J=8.4 Hz, 3H), 3.90-2.90 (m, 61H), 2.20-2.00 (t, 2H), 1.95 (s, 9H), 1.65-1.10 (m, 36H).

$^{13}$C NMR ($D_2O$, 75 MHz): δ 176.67, 175.10, 174.47, 170.84, 101.55, 75.00, 70.98, 70.17, 67.76, 65.24, 60.88, 58.34, 58.17, 57.70, 55.56, 55.15, 52.41, 51.48, 51.19, 50.50, 42.29, 39.35, 39.39, 35.67, 28.45, 28.34, 28.09, 25.63, 25.57, 25.07, 24.68, 22.80, 22.21.

MALDI-TOF: m/z 1850.87 $(M+Na)^+$, 1866.84 $(M+K)^+$.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method for preparing a precursor containing trisaccharide and DTPA ligand, said method comprising the steps of:

(1) coupling 6-aminohexanol (ah) to N-Carbobenzyloxyglycine (Z-G), generating an amide bond and forming a compound Z-G-ah;

(2) joining Z-G-ah with GalNAc(OAc)₄ in a solvent with a catalyst; the catalyst is boron trifluoride etherate or trimethylsiliyltriflouromethanesulfonate (TMSOTf);

(3) removing an acetyl protecting group by using sodium methoxide to get a compound Z-G-ah-GalNAc and then using a silica gel column for separation and purification;

(4) hydrogenizing the compound Z-G-ah-GalNAc to remove carboxybenzyl and obtain a compound G-ah-GalNAc;

(5) coupling N^α,N^α-bis(carboxymethyl)-L-lysine hydrate to benzyl chloroformate to form a compound Z-DCM-Lys (ε-benzyloxycarbonyl-α-dicarboxylmethyl-L-lysine);

(6) coupling the compound G-ah-GalNAc to the compound Z-DCM-Lys, generating an amide bond and obtaining a compound Z-DCM-Lys(G-ah-GalNAc)₃; then adding diethyl ether to make the compound Z-DCM-Lys(G-ah-GalNAc)₃ precipitate out and purifying the compound Z-DCM-Lys(G-ah-GalNAc)₃ by liquid chromatographic column;

(7) hydrogenizing the compound Z-DCM-Lys(G-ah-GalNAc)₃ to remove carboxybenzyl and get a compound DCM-Lys(G-ah-GalNAc)₃;

(8) coupling the compound DCM-Lys(G-ah-GalNAc)₃ to N-Benzyloxycarbonyl-6-aminohexanoic acid (Z-aha) and then hydrogenizing again for removing carboxybenzyl to get a compound aha-DCM-Lys(G-ah-GalNAc)₃;

(9) coupling the compound aha-DCM-Lys(G-ah-GalNAc)₃ to a DTPA-dianhydride and get a compound DTPA-aha-DCM-Lys(G-ah-GalNAc)₃;

next using a liquid chromatographic column for separation and purification of the compound DTPA-aha-DCM-Lys(G-ah-GalNAc)₃; a structural formula of DTPA-aha-DCM-Lys(G-ah-GalNAc)₃ is:

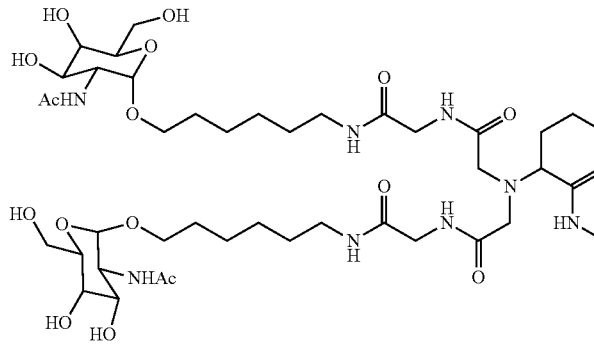
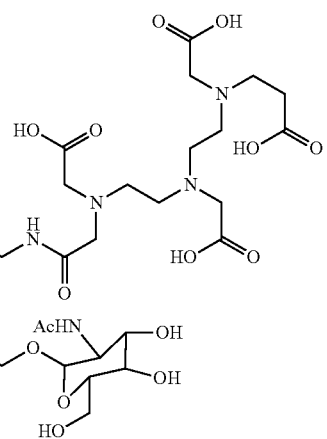

DTPA-aha-DCM-Lys(G-ah-GalNAc)$_3$; is a precursor for labeling hepatocyte receptors and containing trisaccharide and DTPA ligand;

wherein the liquid chromatographic columns for separation and purification are C18 reversed phase columns (RP-18 column).

2. The method as claimed in claim 1, wherein the solvent is anhydrous nitromethane or dichloromethane.

3. The method as claimed in claim 1, wherein before adding diethyl ether to the compound Z-DCM-Lys(G-ah-GalNAc)3 of the step 6, the step 6 further includes steps of dissolving the compound G-ah-GalNAc and the compound Z-DCM-Lys in anhydrous N,N-dimethylformamide (DMF);

adding N-Hydroxybenzotrizole (HOBt), and N,N-Diisopropylethylamine (DIEA) into solution; cooling solution temperature to 0 degree Celsius (° C.) and then adding 1-(3-Dimethylaminopropyl)-3-ethylcarbodiimide (EDCI) into solution.

4. The method as claimed in claim 1, wherein after the step of using liquid chromatographic columns for separation and purification, a freezer dryer is used for drying.

5. The method as claimed in claim 1, wherein in the step 9 coupling the compound aha-DCM-Lys (G-ah-GalNAc)$_3$ to a DTPA-dianhydride, a solvent is added.

6. The method as claimed in claim 5, wherein the solvent is saturated sodium bicarbonate aqueous solution.

7. The method as claimed in claim 1, wherein the compound DTPA-aha-DCM-Lys(G-ah-GalNAc)$_3$ further bonds to a radioactive isotope or a magnetic metal to get a radiotracer of the precursor used for labeling hepatocyte receptors and containing trisaccharide and DTPA ligand.

8. The method as claimed in claim 7, wherein the radioactive isotope is selected from the group consisting of $^{99m}$Tc, $^{68}$Ga and $^{111}$In.

9. The method as claimed in claim 7, wherein the magnetic metal is a gadolinium ion of the magnetic metal or a iron group ion of the magnetic metal.

* * * * *